(12) United States Patent
Reidenberg et al.

(10) Patent No.: US 7,413,748 B2
(45) Date of Patent: *Aug. 19, 2008

(54) TRANSDERMAL BUPRENORPHINE TO TREAT PAIN IN SICKLE CELL CRISIS

(75) Inventors: Bruce E. Reidenberg, Rye, NY (US); Daniel A. Spyker, Burlingame, CA (US)

(73) Assignee: Purdue Pharma L.P., Stamford, CT (US)

( * ) Notice: Subject to any disclaimer, the term of this patent is extended or adjusted under 35 U.S.C. 154(b) by 537 days.

This patent is subject to a terminal disclaimer.

(21) Appl. No.: 10/736,049

(22) Filed: Dec. 15, 2003

(65) Prior Publication Data

US 2004/0126417 A1 Jul. 1, 2004

Related U.S. Application Data

(60) Provisional application No. 60/433,208, filed on Dec. 13, 2002.

(51) Int. Cl.
*A61F 13/00* (2006.01)
(52) U.S. Cl. .................................................. 424/449
(58) Field of Classification Search ................. 424/443, 424/449; 514/282
See application file for complete search history.

(56) References Cited

U.S. PATENT DOCUMENTS

| | | | |
|---|---|---|---|
| 4,582,835 A * | 4/1986 | Lewis et al. ................. 514/282 |
| 4,784,855 A * | 11/1988 | Yamashita et al. .......... 424/436 |
| 4,806,341 A | 2/1989 | Chien et al. |
| 5,026,556 A | 6/1991 | Drust et al. |
| 5,069,909 A | 12/1991 | Sharma et al. |
| 5,149,538 A | 9/1992 | Granger et al. |
| 5,225,199 A | 7/1993 | Hidaka et al. |
| 5,240,711 A | 8/1993 | Hille et al. |
| 5,613,958 A | 3/1997 | Kochinke et al. |
| 5,968,547 A | 10/1999 | Reder et al. |
| 6,595,956 B1 * | 7/2003 | Gross et al. ................ 604/141 |
| 2002/0137761 A1 * | 9/2002 | Crain et al. ................ 514/282 |
| 2003/0104976 A1 * | 6/2003 | Davar et al. ................ 514/1 |

OTHER PUBLICATIONS

International Search Report, PCT/US03/39793, filed Mar. 31, 2004, 2 pages.*
Adrianensen et al., Acta Anaesthesiol Belg 1985;36:33-40.
Brema et al., Int J Clin Pharmacol Res 1996;16:109-116.
Capogna et al., Anaesthesia 1988, 43:128-130.
Hale et al., Abstract, 08 GSA 2001.
Hale et al., Abstract, Nat'l Clin. Symposium of the American College of Nurse Practitioners; Oct. 2001.
Hale et al., J. Clin. Pharmacol. 2001; 41(9):1027, Abstract 58.
Inagaki et al., Anesth Analg 1996;83:530-536.
Nasar et al., Curr Med Res Opin 1986;10:251-255.
Oda et al., Br. J. Anaesthesia 1999;82(6):900-903.
Reidenberg et al., J. Clin. Pharmacol. 2001;41(9):1027, Abstract 57.
Spyker et al., J. Amer. Geriatrics Soc. 2002;50(4):S66, Abstract P162.
Spyker et al., J. Pain 2002;3(2, Suppl. 1):12, Abstract 645.
Spyker et al., J. Pain 2002;3(2, Suppl 1):14, Abstract 653.
Spyker et al., Clin. Pharmacol. Ther. 2000;67(2):145, Abstract PIII-12.
Spyker et al., Clin. Pharmacol. Ther. 2001;69(2):P33, Abstract PII-3.
Spyker et al., Conference Abstract presented on Oct. 15, 2001.
Tauzin-Fin et al., Eur J Anaesthesiol 1998;15:147-152.
Eke et al., Tropical Medicine and International Health 2000;5:81-84.
Griffin et al., N Engl J Med 1994;330:733-7.
Woods et al., J Assoc Acad Minor Phys 1990;1(3):90-2.
Yaster et al., Peditr Clin North Am 2000;47:699-710.
Yaster et al., Pediatrics 1994;93(2):310-5.
Editorial Buprenorphine for Depression: The Un-adoptable Orphan, 1996 Society of Biological Psychiatry 1996; 36:989-990.
Expert Opinion Ther. Targets (2007) 11(2):145-159; F. Noble & B. P. Rogues.
Psychopharmacology (2006) 188:111-118; E. Berrocoso, M. O. Rojas-Corrales, J. A. Mico

* cited by examiner

*Primary Examiner*—Sharon E. Kennedy
(74) *Attorney, Agent, or Firm*—Darby & Darby

(57) ABSTRACT

A specific dosage regimen of buprenorphine achieves pain relief from painful episodes due to sickle cell disease. The dosage regimen comprises administering to a patient in need of pain relief from sickle cell disease at least one BTDS transdermal patch. Alternatively, the dosing regimen comprises administering to the patient (1) a first buprenorphine-containing transdermal dosage form for a first dosing period; (2) administering to the patient a second buprenorphine-containing transdermal dosage form for a second dosing period, where the second dosage form comprises the same dosage of buprenorphine as, or a greater dosage of buprenorphine than, the first dosage form; and (3) administering to the patient a third buprenorphine-containing transdermal dosage form for a third dosing period, where the third dosage form comprises a greater dosage of buprenorphine than the second dosage form.

60 Claims, No Drawings

TRANSDERMAL BUPRENORPHINE TO TREAT PAIN IN SICKLE CELL CRISIS

This application claims the benefit of U.S. provisional application No. 60/433,208, filed Dec. 13, 2002, which is incorporated by reference herein in its entirety.

FIELD OF THE INVENTION

The present invention relates to the treatment of pain symptoms associated with sickle cell disease. In particular, the invention relates to a method of treating pain associated with these conditions by administering a series of buprenorphine transdermal dosage forms.

BACKGROUND OF THE INVENTION

Sickle cell disease a hemolytic disorder, which affects, in its most severe form, approximately 80,000 patients in the United States (see, for example, D. L. Rucknagel, in R. D. Levere, Ed., Sickle Cell Anemia and Other Hemoglobinopathies, Academic Press, New York, 1975, p. 1). Sickle cell disorders are inherited disorders of the haemoglobin (Hb) in the red blood cells. It includes Sickle Cell Anemia (Hb SS), Hemoglobin SC Disease (Hb SC) and Sickle Beta Thalassaemia (Hb Beta-Thal). Of these, the most common and severe is sickle cell anemia.

Sickle cell anemia is caused by a single mutation in the hemoglobin molecule; β6 glutamic acid in normal adult hemoglobin A is changed to valine in sickle hemoglobin S (Ingram, Nature 1956, 178:792-794). Hemoglobin S has a markedly decreased solubility in the deoxygenated state when compared to that of hemoglobin A. Therefore, upon deoxygenation, hemoglobin S molecules within the erythrocyte tend to aggregate and form helical fibers that cause the red cell to assume a variety of irregular shapes, most commonly in the sickled form. After repeated cycles of oxygenation and deoxygenation, the sickle cell in the circulation becomes rigid and no longer can squeeze through the small capillaries in tissues, resulting in delivery of insufficient oxygen and nutrients to the organ, which eventually leads to local tissue necrosis. The prolonged blockage of microvascular circulation and the subsequent induction of tissue necrosis lead to various symptoms of sickle cell anemia, including painful crises of vaso-occlusion.

Hemoglobin SC disease (Hb SC) and Sickle Beta-Thalassaemia (Hb S-Thal) occur when someone inherits sickle hemoglobin (Hb S) from one of their parents and either hemoglobin C or Beta-Thalassaemia from the other parent. The symptoms of these two conditions are often similar to, but usually less severe than, those of sickle cell anemia.

For most patients, sickle cell anemia does not cause chronic pain. However, most sickle cell anemia patients suffer from sporadic and recurrent episodes that are referred to as painful episodes. Painful episodes typically involve blockade of capillaries and prevention of blood flow into a tissue, which becomes starved of oxygen and glucose. During such crises, a sickle cell (SC) patient will usually experience severe pain at one or more locations, which frequently vary between patients. It is not uncommon for a joint or joints to become swollen and sore. By far the most common type of crisis is the infarctive or painful crisis, characterized by severe skeletal pain which may persist for several days or even weeks. In addition, or alternatively, the patient may suffer from either sharp or diffuse pain in the abdomen, which is presumed to be due to ischemic conditions in one or more organs.

Most sickle cell patients usually suffer several painful episodes per year. The patient usually must be hospitalized for parenteral opioid analgesia, restricted to bed rest with little or no exertion to prevent pathological fracture of potentially infarcted bone, and treated with a variety of drugs, including potent analgesics, such as morphine, codeine, and meperidine (also known as Demerol™), and by broad-spectrum antibiotics, both to help control any infections that may be contributing to the crises, and to help prevent or reduce additional infections in tissues or organs that are weakened by the ischemic crisis. Among hospitalizations including the diagnosis of sickle cell disease, 25% of patients are less than 15 years old.

The physiological damage and increased morbidity and mortality caused by sickle cell anemia has been studied extensively (Platt et al., NEJM 1994, 3 30:1639-1644). Briefly, among young children, dactylitis is common, due to ischemic necrosis of the small bones and cartilages of the hands and feet, and acute abdominal pain is often caused by accumulating damage to the spleen. Acute abdominal pain can also be due to spleen, liver or kidney infarction, or the pain can be simply associated with hematuria.

A treatment for sickle cell anemia that has shown benefit involves a compound called hydroxyurea. In some patients, this compound can reduce the frequency, but not the severity, of sickle cell crises, presumably due to an ability to increase the expression levels of fetal hemoglobin genes. However, this treatment has only limited utility; many patients on hydroxyurea still experience recurrent painful episodes, and it is not effective in treating those episodes.

While several innovative pharmacologic approaches to analgesia in this setting have been suggested, including Nalbuphine (Woods et al., J Assoc Acad Minor Phys 1990, 1(3): 90-2); epidural bupivicaine and intravenous fentanyl (Yaster et al. Pediatrics 1994, 93(2):310-5); high dose methylprednisolone and morphine (Griffin et al., N Engl J Med 1994; 330:733-7); and Piroxicam (Eke et al., Tropical Medicine and International Health 2000, 5:81-84), there is still a need for improved modalities of analgesic care of sickle cell disease (Yaster et al., Peditr Clin North Am 2000; 47: 699-710).

There remains a need for safe and effective methods of pain management for sickle cell patients, including pediatric patients. These and other objects of the invention will become more apparent through the following summary, drawings, and description of the preferred embodiments.

SUMMARY OF THE INVENTION

The present invention provides specific dosage regimens of buprenorphine that enables effective analgesia or pain relief from painful episodes due to sickle cell disease.

Accordingly, the invention provides a method of treating a painful episode due to sickle cell disease in a patient by administering a buprenorphine transdermal system (BTDS). Preferably, the transdermal system is administered within two days after the onset of the painful episode. The administering of the BTDS preferably results in a reduction of the pain experienced by the patient by at least 1 point on an 11 point pain scale, such as a Likert-type pain scale. The BTDS can be removed, for example, 7 days after administration. In a p articular embodiment, the BTDS is BTDS 5. The BTDS can be a single patch for the duration of the entire episode, or a single dose for one or more seven-day periods, or, if more than one BTDS is used, a change in dose with each new BTDS.

The invention also provides a method of treating painful episodes due to sickle cell disease in a patient comprising administering to the patient: (1) a first buprenorphine-containing transdermal dosage form for a first dosing period; (2) a second buprenorphine-containing transdermal dosage form for a second dosing period, the second dosage form comprising the same or greater dosage of buprenorphine than the first dosage form; and (3) a third buprenorphine-containing transdermal dosage form for a third dosing period, the third dosage form comprising the same or greater dosage of buprenorphine than the second dosage form.

Preferably, the first and second dosing periods are each at least 2 days. Preferably, the third dosing period is at least 5 days. In a specific embodiment, the first dosage form comprises 5 mg of buprenorphine. In another embodiment, the second dosage form comprises 10 mg of buprenorphine. In other embodiments, the third dosage form comprises 20, 30, or 40 mg of buprenorphine. Optionally, the method of the invention further comprises a fourth dosage period at least once after the third dosing period until pain relief is achieved. One preferred embodiment is where the first dosage comprises BTDS 5 for a dosing period of 3 days, the second dosage comprises BTDS 10 for a dosing period of 3 days, and a third dosage comprises BTDS 20 for a dosing period of 7 days. In yet another embodiment a fourth dosage form of BTDS 10 or BTDS 20 is administered at least once after the third dosage period every 7 days.

The invention also provides for a method of treating a painful episode due to sickle cell anemia in a patient comprising administering intravenously to the patient an effective amount of an opioid for an initial part of the painful episode; and administering to the patient at least one BTDS for the remainder of the painful episode, while reducing the amount of the opioid administered intravenously. Preferably, the initial administration is no more than 3 days. In a specific embodiment, at least one BTDS is a BTDS 5. In one preferred embodiment, at least one BTDS comprises a BTDS 5 for 3 days; a BTDS 10 for 3 days; and a BTDS 20 for 7 days. The opioid administered during the initial part of the episode may be selected from, but is not limited to, buprenorphine, morphine, hydromorphone, oxycodon, tramadol, oxymorphone, dihydrocodein, and hydrocodon.

In particular embodiments, the patient suffering from sickle cell disease is pediatric or adult. Conditions where painful episodes occur due to sickle cell disease include, but are not limited to, sickle cell anemia, hemoglobin SC disease or hemoglobin S-β-thalassemia. The transdermal administration can be produced by a transdermal dosage article, preferably a diffusion-driven transdermal system. Alternatively, the transdermal administration can be produced by a transdermal system selected from a topical gel, a lotion, an ointment, a transmucosal system, a transmucosal device, and an iontophoretic delivery system.

DETAILED DESCRIPTION OF THE INVENTION

The present invention provides a method of achieving effective treatment of pain in a patient having sickle cell anemia in need of such treatment quickly, while minimizing certain adverse effects. In addition, the invention provides a treatment regimen for an extended time period to address the fact that a sickle cell pain episode usually lasts longer than the indicated period for many standard treatments with patient-controlled parenteral analgesia.

The invention is based, in part, on the discovery that transdermal administration of buprenorphine results in blood concentrations of buprenorphine that are useful in treating painful episodes of sickle cell disease.

In addition, the concentrations of buprenorphine provided by BTDS do not induce an opioid blockade, thereby allowing transdermal administration of buprenorphine to be started while the patient is still receiving parenteral opioid medication, without interfering with analgesic effect. Typically, sickle cell patients suffering from a painful episode are given an opioid such as morphine or hydromorphone intravenously after arriving in the E.R. According to the invention, such an i.v. treatment could be tapered off, starting at day 2 or 3 after hospitalization, while at the same time initiating BTDS therapy. Thus, the use of transdermal delivery of buprenorphine can be especially advantageous both as adjuvant pain therapy in the acute pain phase, and as a more definitive therapy as the initial pain wanes.

The method of the invention comprises administering to the patient an analgesically effective amount of buprenorphine in a transdermal dosage regimen including at least one dose level of buprenorphine preferably via BTDS. As used herein, "BTDS" means "Buprenorphine Transdermal System", and "BTDS X", wherein "X" is a number higher than zero, means a transdermal dosage form containing X milligrams of buprenorphine. Thus, for example, "BTDS 5" contains 5 mg buprenorphine. Preferably, a BTDS contains buprenorphine in the form of a base or a salt, more preferably in the form of a base.

As discussed below, the invention provides kits containing the desired dosage series. Such kits may be used in a specific dosage regimen of the present invention, which can be described in terms of administration of a "series of transdermal dosage forms comprising at least one dose level of buprenorphine". A specific dosing regimen involves the application of BTDS 5 for three days, BTDS 10 for three days, and BTDS 20 for seven days. Alternatively, BTDS 5 or 10 may be worn for seven days.

The patient in the present invention is classified as having a sickle cell disease and having pain as a result of the disorder. These patients include but are not limited to those with sickle cell anemia, hemoglobin SC disease or hemoglobin S-β-thalassemia. As used herein the term "sickle cell disease", used interchangeably with the term "sickle cell disorder", refers to a variety of clinical problems attendant upon sickle cell anemia, especially in those subjects who are homozygotes for the sickle cell substitution in hemoglobin. Among the constitutional manifestations included in the term sickle cell disease are delay of growth and development; an increased tendency to develop serious infections, particularly due to pneumococcus; and marked impairment of splenic function, preventing effective clearance of circulating bacteria, with recurrent infarcts and eventual destruction of splenic tissue. Also included in the term "sickle cell disease" are acute episodes of musculoskeletal pain, which affect primarily the lumbar spine, abdomen, and femoral shaft, and which are similar in mechanism and in severity to the bends. In adults, such attacks commonly manifest as mild or moderate bouts of short duration every few weeks or months, interspersed with agonizing attacks lasting 5 to 7 days that strike on average about once a year. Among events known to trigger such crises are acidosis, hypoxia and dehydration, all of which potentiate intracellular polymerization of HbS (J. H. Jandl, Blood: Textbook of Hematology, 2nd Ed., Little, Brown and Company, Boston, 1996, pages 544-545).

In the context of the invention the term "patient" may apply to pediatric patients as well as adults. "A "pediatric" patient or "child" as used herein refers to a person in the age group ranging from birth to sixteen years, including age groups often called neonates, infants, and adolescents.

The patient may be on additional medication to further decrease pain. Such medications include, but are not limited to parenteral, oral or rectal opioids, both mu agonist and partial or mixed agonist/antagonist opioids. As used herein, an "opioid" includes, but is not limited to, buprenorphine, morphine, hydromorphone, oxycodon, tramadol, oxymorphone, dihydrocodein, and hydrocodon. In addition, non steroidal anti-inflammatory drugs (NSAIDS such as ibuprofen and aspirin) and acetominophen can be given to supplement the opioids. The present invention may be used to supplant existing medications, thereby reducing the need for other types of medication.

As used herein, the term "ischemic crises" refers to these sporadic, recurrent crises which occur in the normal course of sickle cell disease; such references do not relate to any other type of ischemic crisis, such as a stroke or heart attack.

An "analgesically effective" amount of an analgesic agent means an amount of agent capable of lowering the level of pain experienced by a patient. The level of pain experienced by a patient can be assessed by use of a visual analog scale (VAS) or a Likert-type scale. A VAS is a straight line with one end of the line representing no pain and the other end of the line representing the worst imaginable pain. Patients are asked to mark on the line where they considered their pain to be at each time point, and the length from no pain to the mark can be related to the length of the full scale. A Likert-type scale is a rating scale, usually in the range of 1 to 5, based on degrees of agreement or disagreement to statements. A similar type of scale, although based on an 11 point scale (ranging from 0 to 10) can also be used. Such pain scales can be applied to visualize an alteration of the level of pain a patient experiences during treatment, e.g., a reduction of the level of pain a patient or a population of patients experiences before and after initiation of a pain therapy.

Buprenorphine

The present invention relates to buprenorphine or a pharmaceutically acceptable salt, ether derivative, ester derivative, acid derivative, enantiomer, diastereomer, racemate, polymorph, or solvate thereof. Pharmacologically, buprenorphine is an opioid partial agonist and shares many of the actions, such as analgesia, of opioid agonists. Partial agonists, generally, include compounds with affinity for a receptor, but unlike full agonists, elicit only a small degree of the pharmacological effect, even if a high proportion of receptors are occupied by the compound. A "ceiling effect" to analgesia (i.e., no additional analgesia with increasing dose) is well documented with respect to buprenorphine in many animal models. It is highly lipophilic and dissociates slowly from opioid receptors. Buprenorphine is considered in the art to be a partial agonist at μ opioid receptors in the central nervous system ("CNS") and peripheral tissues. It is further thought that buprenorphine binds with high affinity to μ and $κ_1$ receptors, and, with lower affinity, to δ receptors. The intrinsic agonist activity at the κ receptor seems to be limited and most evidence suggests that buprenorphine has antagonist activity at κ receptors. The lack of κ agonism accounts for buprenorphine's freedom from the dysphoric and psychotomimetic effects often seen with agonist/antagonist drugs. Other studies suggest that the opioid antagonist effects of buprenorphine may be mediated via an interaction with δ opioid receptors.

It is known in the art that buprenorphine binds slowly with, and dissociates slowly from, the μ receptor. The high affinity of buprenorphine for the μ receptor and its slow binding to, and dissociation from, the receptor is thought to possibly account for the prolonged duration of analgesia, and in part, for the limited physical dependence potential observed with the drug. The high affinity binding may also account for the fact that buprenorphine can block the μ agonist effects of other administered opioids.

Buprenorphine has been shown to be effective to control pain in a wide range of patients when delivered by a number of different routes of administration, including intravenously, epidurally, intrathecally, or sublingually in both young and elderly patients (Inagaki et al., Anesth Analg 1996, 83:530-536; Brema et al., Int J Clin Pharmacol Res 1996, 16:109-116; Capogna et al., Anaesthesia 1988, 43:128-130; Adrianensen et al., Acta Anaesthesiol Belg 1985, 36:33-40; Tauzin-Fin et al., Eur J Anaesthesiol 1998, 15:147-152; Nasar et al., Curr Med Res Opin 1986, 10:251-255).

Like other opioid agonists, buprenorphine produces dose-related analgesia. The exact mechanism has not been fully explained, but analgesia appears to result from a high affinity of buprenorphine for p and possibly K opioid receptors in the central nervous system. The drug may also alter the pain threshold (threshold of afferent nerve endings to noxious stimuli). On a weight basis, the analgesic potency of parenteral buprenorphine appears to be about 25 to about 50 times that of parenteral morphine, about 200 times that of pentazocine, and about 600 times that of meperidine.

Salts and Derivatives

Various pharmaceutically acceptable salts, ether derivatives, ester derivatives, acid derivatives, and aqueous solubility altering derivatives of the active compound also are encompassed by the present invention. The present invention further includes all individual enantiomers, diastereomers, racemates, and other isomers of the compound. The invention also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein.

Suitable salts of the compound include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compound of the present invention.

The present invention includes prodrugs of the compound of the present invention. Prodrugs include, but are not limited to, functional derivatives of buprenorphine that are readily convertible in vivo into buprenorphine. Conventional procedures for the selection and preparation of suitable prodrug derivatives are described, for example, in "Design of Prodrugs", ed. H. Bundgaard, Elsevier, 1985.

Transdermal Dosage Forms

Transdermal dosage forms are convenient dosage forms for delivering many different active therapeutically effective agents, including but not limited to analgesics, such as for example, opioid analgesics. Typical opioid analgesics include, but are not limited to, fentanyl, buprenorphine, etorphines, and other high potency narcotics. Transdermal dosage forms are particularly useful for timed release and sustained release of active agents.

Transdermal dosage forms may be classified into transdermal dosage articles and transdermal dosage compositions. The most common transdermal dosage article is a diffusion-driven transdermal system (transdermal patch) using either a fluid reservoir or a drug-in-adhesive matrix system. Transdermal dosage compositions include, but are not limited to, topical gels, lotions, ointments, transmucosal systems and devices, and iontophoretic (electrical diffusion) delivery systems. Preferably, the transdermal dosage form is a transdermal patch.

Transdermal patch dosage forms used in accordance with the invention preferably include a backing layer made of pharmaceutically acceptable material which is impermeable to the buprenorphine. The backing layer preferably serves as a protective cover for the active agent, e.g. buprenorphine and may also provide a support function. Examples of materials suitable for making the backing layer are films of high and low density polyethylene, polypropylene, polyvinylchloride, polyurethane, polyesters such as poly(ethylene phthalate), metal foils, metal foil laminates of such suitable polymer films, textile fabrics, if the components of the reservoir cannot penetrate the fabric due to their physical properties and the like. Preferably, the materials used for the backing layer are laminates of such polymer films with a metal foil such as aluminum foil. The backing layer can be any appropriate thickness which will provide the desired protective and support functions. A suitable thickness will be from about 10 to about 200 microns. Desirable materials and thickness will be apparent to the skilled artisan.

In certain preferred embodiments, the transdermal dosage forms used in accordance with the invention contain a polymer matrix layer. Generally, the polymers used to form the biologically acceptable polymer matrix are those capable of forming thin walls or coatings through which pharmaceuticals can pass at a controlled rate. A non-limiting list of exemplary materials for inclusion in the polymer matrix includes polyethylene, polypropylene, ethylene/propylene copolymers, ethylene/ethylacrylate copolymers, ethylenevinyl acetate copolymers, silicones, rubber, rubber-like synthetic homo-, co- or block polymers, polyacrylic esters and the copolymers thereof, polyurethanes, polyisobutylene, chlorinated polyethylene, polyvinylchloride, vinyl chloride-vinyl acetate copolymer, polymethacrylate polymer (hydrogel), polyvinylidene chloride, poly(ethylene terephthalate), ethylene-vinyl alcohol copolymer, ethylene-vinyloxyethanol copolymer, silicones including silicone copolymers such as polysiloxane-polymethacrylate copolymers, cellulose polymers (e.g., ethyl cellulose, and cellulose esters), polycarbonates, polytetrafluoroethylene and mixtures thereof. Exemplary materials for inclusion in the polymer matrix layer are silicone elastomers of the general polydimethylsiloxane structures, (e.g., silicone polymers). Preferred silicone polymers cross-link and are pharmaceutically acceptable. Other preferred materials for inclusion in the polymer matrix layer include: silicone polymers that are cross-linkable copolymers having dimethyl and/or dimethylvinyl siloxane units which can be crosslinked using a suitable peroxide catalyst. Also preferred are those polymers consisting of block copolymers based on styrene and 1,3-dienes (particularly linear styrene-isoprene-block copolymers of styrene-butadiene-block copolymers), polyisobutylenes, polymers based on acrylate and/or methacrylate.

The polymer matrix layer may optionally include a pharmaceutically acceptable crosslinking agent. Suitable crosslinking agents include, e.g., tetrapropoxy silane. Preferred transdermal delivery systems used in accordance with the methods of the present invention include an adhesive layer to affix the dosage form to the skin of the patient for a desired period of administration, e.g., about 2 to about 8 days. If the adhesive layer of the dosage form fails to provide adhesion for the desired period of time, it is possible to maintain contact between the dosage form with the skin by, for instance, affixing the dosage form to the skin of the patient with an adhesive tape, e.g., surgical tape. Adhesion of the dosage form to the skin of the patient can be achieved solely by the adhesive layer of the dosage form or in connection with a peripheral adhesive source, such as surgical tape, but the dosage form should preferably be adhered to the patient's skin for the requisite administration period.

The adhesive layer preferably includes using any adhesive known in the art that is pharmaceutically compatible with the dosage form and preferably hypoallergenic, such as polyacrylic adhesive polymers, acrylate copolymers (e.g., polyacrylate) and polyisobutylene adhesive polymers. In other preferred embodiments of the invention, the adhesive is a pressure-sensitive contact adhesive, which is preferably hypoallergenic.

The transdermal dosage forms which can be used in accordance with the present invention may optionally include a permeation enhancing agent. Permeation enhancing agents are compounds which promote penetration and/or absorption of the buprenorphine into the blood stream of the patient. A non-limiting list of permeation enhancing agents includes polyethylene glycols, surfactants, and the like.

Alternatively, permeation of buprenorphine may be enhanced by occlusion of the dosage form after application to the desired site on the patient with, e.g. an occlusive bandage. Permeation may also be enhanced by removing hair from the application site by, e.g. clipping, shaving or use of a depilatory agent. Another permeation enhancer is heat. It is thought that heat enhancement can be induced by, among other things, using a radiating heat form, such as an infrared lamp, onto the application site after application of the transdermal dosage form. Other means of enhancing permeation of buprenorphine such as the use of iontophoretic means are also contemplated to be within the scope of the present invention.

A preferred transdermal dosage form which may be used in accordance with the present invention includes a non-permeable backing layer made, for example, of polyester; an adhesive layer made, for example of a polyacrylate; and a matrix containing the buprenorphine and other desirable pharmaceutical aids such as softeners, permeability enhancers, viscosity agents and the like.

The active agent, buprenorphine, may be included in the device in a drug reservoir, drug matrix or drug/adhesive layer.

This area of the patch, and the amount of active per unit area determine the limit dose, as one of ordinary skill in the art can readily determine.

Certain preferred transdermal delivery systems also include a softening agent. Suitable softening agents include higher alcohols such as dodecanol, undecanol, octanol, esters of carboxylic acids, wherein the alcohol component may also be a polyethoxylated alcohol, diesters of dicarboxylic acids, such as di-n-butyladiapate, and triglycerides particularly medium-chain triglycerides of the caprylic/capric acids or coconut oil, have proved to be particularly suitable. Further examples of suitable softeners are multivalent alcohols, for example, levulinic acid, cocprylic acids glycerol and 1,2-propanediol which can also be etherified by polyethylene glycols.

A buprenorphine solvent may also be included in the transdermal delivery systems of the present invention. Preferably, the solvents dissolve the buprenorphine to a sufficient extent thereby avoiding complete salt formation. A non-limiting list of suitable solvents include those with at least one acidic group. Particularly suitable are monoesters of dicarboxylic acids such as monomethylglutarate and monomethyladipate.

Other pharmaceutically acceptable compounds which may be included in the reservoir or matrix include: solvents, for example alcohols such as isopropanol; permeation enhancing agents such as those described above; and viscosity agents, such as cellulose derivatives, natural or synthetic gums, such as guar gum, and the like.

In preferred embodiments, the transdermal dosage form includes a removable protective layer. The removable protective layer is removed prior to application, and consists of the materials used for the production of the backing layer described above provided that they are rendered removable, for example, by a silicone treatment. Other removable protective layers, for example, are polyletra-fluoroethylene, treated paper, allophane, polyvinyl chloride, and the like. Generally, the removable protective layer is in contact with the adhesive layer and provides a convenient means of maintaining the integrity of the adhesive layer until the desired time of application.

The composition of the transdermal dosage forms used in accordance with the invention and the type of device used are not considered critical to the method of the invention, provided that the device delivers the active agent, e.g. buprenorphine, for the desired time period and at the desired flux rate and/or the desired delivery rate of the transdermal dosage form.

Certain preferred transdermal dosage forms for use in accordance with the present invention are described in U.S. Pat. No. 5,240,711 to Hille, et. al.; (assigned to LTS Lohmann Therapie-Systeme GmbH & Co.), hereby incorporated by reference. Such buprenorphine transdermal delivery systems may be a laminated composite having an impermeable backing layer containing buprenorphine, and optionally, a permeation enhancer combined with a pressure-sensitive adhesive. A preferred transdermal dosage form in accordance with the U.S. Pat. No. 5,240,711 patent includes: (i) a polyester backing layer which is impermeable to buprenorphine; (ii) a polyacrylate adhesive layer; (iii) a separating polyester layer; and (iv) a matrix containing buprenorphine, a solvent for the buprenorphine, a softener and a polyacrylate adhesive. The buprenorphine solvent may or may not be present in the final formulation. The transdermal delivery device described therein includes a backing layer which is impermeable to the active substance, a pressure-sensitive adhesive reservoir layer and optionally, a removable protective layer. Preferably, the reservoir layer includes about 10 to about 95% (by weight) polymeric material, about 0.1 to about 40% (by weight) softener, about 0.1 to about 30% (by weight) buprenorphine. A solvent for the buprenorphine base or pharmaceutically acceptable salt thereof may be included as about 0.1 to about 30% (by weight).

Transdermal delivery systems of buprenorphine, made by Lohmann Therapie-Systeme GmbH & Co., are currently sold in the European Union under the trademark name TRANSTEC®. These patches contain 20, 30, and 40 mg of buprenorphine, with an approximate delivery or "flux" rate of 35, 52.5, and 70 µg/hr, respectively. There are several other types of transdermal formulations of buprenorphine reported in the literature. See, for example, U.S. Pat. No. 5,240,711 to Hille et al., U.S. Pat. No. 5,225,199 to Hidaka et al., U.S. Pat. No. 5,069,909 to Sharma et al., U.S. Pat. No. 4,806,341 to Chien et al.; U.S. Pat. No. 5,026,556 to Drust et al.; U.S. Pat. No. 5,613,958 to Kochinke et al.; and U.S. Pat. No. 5,968,547 to Reder et al.

The dosage forms of the present invention may also include one or more inactivating agents. The term "inactivating agent" refers to a compound that inactivates or crosslinks the active agent, in order to decrease the abuse potential of the transdermal dosage form. Non limiting examples of a inactivating agents include, but are not limited to, polymerizing agents, photinitiators, and formalin. Examples of polymerizing agents include diisocyanates, peroxides, diimides, diols, triols, epoxides, cyanoacrylates, and UV activated monomers.

Any additional suitable additives, inactivating agents, and dosage forms that are known in the art may be used in combination with the method of the invention.

Topical preparations typically contain a suspending agent and optionally, an antifoaming agent. Such topical preparations may be liquid drenches, alcoholic solutions, topical cleansers, cleansing creams, skin gels, skin lotions, and shampoos in cream or gel formulations (including, but not limited to aqueous solutions and suspensions).

The compound of the present invention also can be administered in the form of liposome delivery systems, such as small unilamellar vesicles, large unilamellar vesicles and multilamellar vesicles that may be included in the transdermal article or transdermal composition. Liposomes can be formed from a variety of phospholipids, such as cholesterol, stearylamine or phosphatidylcholines.

The transdermal dosage form may be formulated by any method known in the art and may be administered as suggested. Such formulations are described in U.S. Pat. Nos. 4,806,341; 5,240,711; and 5,968,547.

Administration

The unit dosage forms of the present invention are administered to a patient suffering from pain associated with painful episodes from sickle cell anemia.

Pain relief can be achieved by providing either a single BTDS dosage for the duration of a painful episode, primarily in episodes of low to moderate length and intensity, or by rapidly escalating the dose to an effective dose. In the latter case, the unit dosage forms of the present invention may be administered according to a defined dosing regimen in order to obtain optimal activity while minimizing any potential adverse effects or toxicity.

For example, the method can involve administering to the patient an analgesic effective amount of buprenorphine in a regimen comprising administering to the patient a series of transdermal dosage forms comprising graduated and ascending (or descending) dosages of buprenorphine.

Preferably, the dosage regimen comprises the steps of:

(a) administering to the patient a first buprenorphine-containing transdermal dosage form for a first dosing period;

(b) administering to the patient a second buprenorphine-containing transdermal dosage form for a second dosing period, wherein the second dosage form comprises the same or a greater dosage of buprenorphine than the first dosage form; and (c) administering to the patient a third buprenorphine-containing transdermal dosage form for a third dosing period, wherein the third dosage form comprises a greater dosage of buprenorphine than the second dosage form.

The dosing regimen of the present invention comprises several discrete dosing periods. A dosing period is the time during which one of the transdermal dosage forms in the series is administered to the patient, and the dosing regimen will consist of a separate dosing period for administration of each transdermal dosage form in the series. Thus, for example, the first transdermal dosage form in the series may be worn by the patient for three consecutive days, although periods of from two to seven days are contemplated. Preferably, although not necessarily, the patch is placed at the mid-axillary line at the fifth intercostal space. Upon removal, the second dosage form may then be worn by the patient for another three consecutive days (or from two to seven days), and thereafter, the third dosage form maybe worn by the patient for another seven days. In a preferred embodiment, the total treatment period of the dosing regimen is six days until the desired dose is attained. This dose can then be maintained indefinitely. If an increase in dosage is required, then the dosage may be increased at an appropriate interval, e.g., every three to seven days.

In one embodiment, the BTDS dose escalation regimen is designed to escalate the buprenorphine dose until the patient experiences effective pain relief, and the patient thereafter maintained on the effective BTDS dose level. Pain intensity and/or pain relief is advantageously evaluated using a scoring system such as the Memorial Pain Assessment Card (Fishman et al., Cancer 1987;60:1151-8). For example, these parameters may be assessed by the patient using an 11 point scale anchored at 0 with "no pain at all" and at 10 with "worst possible pain." Preferably, pain intensity is assessed prior to application of the BTDS 5, within 15 minutes after application of BTDS 5, and thereafter at suitable intervals during the dose escalation period. For example, pain intensity and pain relief can be assessed 3 times daily while the patient is hospitalized, and once daily (evening) when the patient is an outpatient.

In a specific embodiment the first dosage form comprises up to 5 mg buprenorphine, the first dosing period is at least 2 days, the second dosage form comprises up to 10 mg buprenorphine, the second dosing period is at least 3 days; the third dosage form comprises up to 20 mg buprenorphine, and the third dosing period is 2-3 days. In an alternative embodiment, subsequent dosages may be administered every 7 days. If the target analgesia level is attained with the second or third dosing period, the second or third dosage form can be continually administered for an indefinite period of time, changing patches with a frequency extending from about every 2 days to weekly. If the target analgesia level is not attained with the third dosing period, subsequent dosage forms can be used incrementally starting with 30 mg buprenorphine and 40 mg buprenorphine load.

In an alternative embodiment, a dosage form of BTDS, such as BTDS 10, may be administered for 7 days, and continued thereafter every 7 days.

The invention also contemplates reducing the dosage level if the patient response seems to warrant a reduction in dose. The time periods for a reduced dose are the same as for maintained or increased dosages.

The dosage of the compound of the present invention may vary according to a variety of factors such as underlying disease states, the individual's condition, weight, sex and age and the mode of administration. The dosage predefined interval or regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the absorption, distribution, metabolism, and excretion of a drug.

The composition or dosage form of the invention, when administered as a transdermal dosage form, may be provided to any body part as determined by one of ordinary skill in the art. For example, the composition or dosage form may be provided to the arm, leg or chest of the patient. In the preferred embodiment for children, the placement is preferably on the back to prevent the removal of the transdermal unit by the patient. Repeated doses may not be administered to the same location each time. Preferably, if the dosages are to be administered to the same location, a one month interval will have lapsed prior to using the same location.

Generally, topical preparations contain from about 0.01 to about 100% by weight and preferably from about 3 to about 80% by weight of the compound, based upon 100% total weight of the topical preparation. Generally, transdermal dosage forms contain from about 0.01 to about 100% by weight and preferably from about 3 to about 50% by weight of the compound, based upon 100% total weight of the dosage.

The dosage forms used in the method of the present invention may be administered alone or in combination with other active agents. For combination treatment with more than one active agent, where the active agents are in separate dosage formulations, the active agents can be administered concurrently, or they each can be administered at separately staggered times. The dosage amount may be adjusted when combined with other active agents as described above to achieve desired effects. On the other hand, unit dosage forms of these various active agents may be independently optimized and combined to achieve a synergistic result wherein the pathology is reduced more than it would be if either active agent were used alone.

Kits

The present invention also provides an embodiment wherein the components for practicing the invention can be conveniently provided in a kit form. In its simplest embodiment, a kit of the invention provides a set number of buprenorphine patches at set dosages, wherein the dosages are set according to the needs of the patient. Preferred kits include, but are not limited to, the dosage regimens selected from the following table.

| Amount of Buprenorphine per Transdermal Dosage Form (mg) | | |
|---|---|---|
| First | Second | Third |
| 5 | 10 | 20 |
| 10 | 10 | 10 |
| 5 | 10 | 10 |
| 5 | 20 | 20 |

In a preferred embodiment, the dosage regimen is BTDS 5 for 3 days, BTDS 10 for 3 days, and BTDS 20 for 7 days.

In a preferred embodiment, the kit will include subsequent patches as necessary for the patient (BTDS 5, 10, 20, 30, or 40). Instructions on how to apply the patch, storage of the unit, and details of the treatment regimen are also included.

In a further embodiment, the kit will include a disposal container or device for disposal of used buprenorphine patches. Such containers or devices can be used to prevent or limit potential abuse of the drug within the patch. As used herein, the term container has its broadest meaning, i.e., any receptacle for holding material.

A kit of the invention preferably includes packaging and instructions for its use, e.g., on the packaging or package insert. The buprenorphine patches within the kit may be coded (i.e., color, numerical by day, or numerical by dose, etc.) for the patient.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, procedures, and the like are cited throughout this application, the disclosures of which are incorporated herein by reference in their entireties.

What is claimed is:

1. A method of treating a painful episode due to sickle cell disease in a patient in need of such treatment, which method comprises administering to the patient a buprenorphine transdermal system (BTDS) as a monotherapy treatment.

2. The method of claim 1, comprising administering BTDS 5 within two days after the onset of the painful episode.

3. The method of claim 1, wherein the administering of the BTDS results in a reduction of the pain experienced by the patient by at least 1 point on an 11 point pain scale.

4. A method of treating a painful episode due to sickle cell disease in a patient in need of such treatment, which method comprises:
administering to the patient a first buprenorphine-containing transdermal dosage form as a monotherapy treatment for a first dosing period;
administering to the patient a second buprenorphine-containing transdermal dosage form as a monotherapy treatment for a second dosing period, wherein the second dosage form comprises the same dosage of buprenorphine as, or a greater dosage of buprenorphine than, the first dosage form; and
administering to the patient a third buprenorphine-containing transdermal dosage form as a monotherapy treatment for a third dosing period, wherein the third dosage form comprises a greater dosage of buprenorphine than the second dosage form.

5. The method of claim 4, further comprising extended subsequent dosing periods with subsequent dosage forms for a given time period as needed by the patient to achieve desired analgesia.

6. The method of claim 4, wherein the first dosing period is at least 2 days.

7. The method of claim 4, wherein the second dosing period is at least 2 days.

8. The method of claim 4, wherein the third dosing period is at least 5 days.

9. The method of claim 4, wherein the first dosage form comprises 5 mg of buprenorphine.

10. The method of claim 4, wherein the second dosage form comprises 10 mg of buprenorphine.

11. The method of claim 4, wherein the third dosage form comprises 20 mg of buprenorphine.

12. The method of claim 4, wherein the third dosage form comprises 30 mg of buprenorphine.

13. The method of claim 4, wherein the third dosage form comprises 40 mg of buprenorphine.

14. A method of treating a painful episode due to sickle cell anemia in a patient in need of such treatment, which method comprises:
administering to the patient BTDS 5 as a monotherapy treatment for 3 days;
administering to the patient BTDS 10 as a monotherapy treatment for 3 days; and
administering to the patient BTDS 20 as a monotherapy treatment for 7 days.

15. The method of claim 14, further comprising extended subsequent dosing periods with subsequent BTDS 20 dosage forms for a given time period as needed by the patient to achieve desired analgesia.

16. A method of treating a painful episode due to sickle cell anemia in a patient in need of such treatment, which method comprises administering to the patient BTDS 10 as a monotherapy treatment for 7 days with subsequent BTDS 20 as a monotherapy treatment dosage forms for a given time period as needed by the patient to achieve desired analgesia.

17. The method of claim 1, wherein the patient is a child.

18. The method of claim 1, wherein the patient is an adult.

19. The method of claim 1, wherein the sickle cell disease is sickle cell anemia.

20. The method of claim 1, wherein the sickle cell disease is hemoglobin SC disease or hemoglobin S-β-thalassemia.

21. The method of claim 1, wherein the transdermal dosage form is selected form the group consisting of transdermal dosage article and transdermal dosage composition.

22. The method of claim 21, wherein the transdermal dosage article is a diffusion-driven transdermal system.

23. The method of claim 21, wherein the transdermal dosage composition is selected from the group consisting of a topical gel, a lotion, an ointment, a transmucosal system, a transmucosal device, and an iontophoretic delivery system.

24. A method of treating a painful episode due to sickle cell anemia in a patient in need of such treatment, which method comprises
administering intravenously to the patient an effective amount of opioid for an initial part of the painful episode; and administering to the patient at least one BTDS as a monotherapy treatment for the remainder of the painful episode, while reducing the amount of the opioid administered intravenously.

25. The method of claim 24, wherein the initial part is no more than 3 days.

26. The method of claim 24, wherein the at least one BTDS is a BTDS 5.

27. The method of claim 24, wherein the at least one BTDS comprises a BTDS 5 for 3 days; a BTDS 10 for 3 days; and a BTDS 20 for 7 days.

28. The method of claim 24, wherein the opioid is a member of the group consisting of buprenorphine, morphine, hydromorphone, oxycodon, tramadol, oxymorphone, dihydrocodein, and hydrocodon.

29. A method of treating a painful episode due to sickle cell disease in a patient in need of such treatment, which method comprises administering to the patient a buprenorphine transdermal system (BTDS) in combination with a mu agoinst opioid or a mixed agonistlantagonist opioid.

30. The method of claim 29, which comprises administering BTDS 5 within two days after the onset of the painful episode.

31. The method of claim 29, which further comprises:
administering to the patient a first buprenorphine-containing transdermal dosage form for a first dosing period;
administering to the patient a second buprenorphine-containing transdermal dosage form for a second dosing period, wherein the second dosage form comprises the same dosage of buprenorphine as, or a greater dosage of buprenorphine than, the first dosage form; and
administering to the patient a third buprenorphine-containing transdermal dosage form for a third dosing period, wherein the third dosage form comprises a greater dosage of buprenorphine than the second dosage form.

32. The method of claim 31, which further comprises administering subsequent dosing periods with subsequent buprenorphine dosage forms for a given time period as needed by the patient to achieve analgesia.

33. The method of claim 31, wherein the first dosing period is at least 2 days.

34. The method of claim 31, wherein the second dosing period is at least 2 days.

35. The method of claim 31, wherein the third dosing period is at least 5 days.

36. The method of claim 31, wherein the first dosage form comprises 5 mg of buprenorphine.

37. The method of claim 31, wherein the second dosage form comprises 10 mg of buprenorphine.

38. The method of claim 31, wherein the third dosage form comprises 20 mg of buprenorphine.

39. The method of claim 31, wherein the third dosage form comprises 30 mg of buprenorphine.

40. The method of claim 31, wherein the third dosage form comprises 40 mg of buprenorphine.

41. A method of treating a painful episode due to sickle cell anemia in a patient in need of such treatment, which method comprises:
administering to the patient BTDS 5 for 3 days;
administering to the patient BTDS 10 for 3 days; and
administering to the patient BTDS 20 for 7 days;
wherein at least one BTDS is administered in combination with a mu agoinst opioid or a mixed agonist/antagonist opioid.

42. The method of claim 41, which further comprises administering subsequent dosing periods with subsequent BTDS 20 dosage forms for a given time period as needed by the patient to achieve analgesia.

43. A method of treating a painful episode due to sickle cell anemia in a patient in need of such treatment, which method comprises administering to the patient BTDS 10 for 7 days with subsequent BTDS 20 dosage forms for a given time period as needed by the patient to achieve desired analgesia, wherein at least one BTDS dosage form is administered in combination with a mu agoinst opioid or a mixed agonistlantagonist opioid.

44. The method of any one of claims 31, 41 or 43, wherein the mu agoinst opioid or mixed agonist/antagonist opioid is selected from the group consisting of: morphine, hydromorphone, oxycodone, tramadol, oxymorphone, dihydrocodeine, and hydrocodone.

45. A method of treating a painful episode due to sickle cell disease in a patient in need of such treatment, which method comprises administering to the patient a buprenorphine transdermal system (BTDS) in combination with a non-steroidal anti-inflammatory drug (NSAID) or acetominophen.

46. The method of claim 45, which comprises administering BTDS 5 within two days after the onset of the painful episode.

47. The method of claim 45, which further comprises:
administering to the patient a first buprenorphine-containing transdermal dosage form for a first dosing period;
administering to the patient a second buprenorphine-containing transdermal dosage form for a second dosing period, wherein the second dosage form comprises the same dosage of buprenorphine as, or a greater dosage of buprenorphine than, the first dosage form; and
administering to the patient a third buprenorphine-containing transdermal dosage form for a third dosing period, wherein the third dosage form comprises a greater dosage of buprenorphine than the second dosage form.

48. The method of claim 45, which further comprises administering subsequent dosing periods with subsequent buprenorphine dosage forms for a given time period as needed by the patient to achieve analgesia.

49. The method of claim 45, wherein the first dosing period is at least 2 days.

50. The method of claim 45, wherein the second dosing period is at least 2 days.

51. The method of claim 45, wherein the third dosing period is at least 5 days.

52. The method of claim 45, wherein the first dosage form comprises 5 mg of buprenorphine.

53. The method of claim 45, wherein the second dosage form comprises 10 mg of buprenorphine.

54. The method of claim 45, wherein the third dosage form comprises 20 mg of buprenorphine.

55. The method of claim 45, wherein the third dosage form comprises 30 mg of buprenorphine.

56. The method of claim 45, wherein the third dosage form comprises 40 mg of buprenorphine.

57. A method of treating a painful episode due to sickle cell anemia in a patient in need of such treatment, which method comprises:
administering to the patient BTDS 5 for 3 days;
administering to the patient BTDS 10 for 3 days; and
administering to the patient BTDS 20 for 7 days;

wherein at least one BTDS is administered in combination with a non-steroidal anti-inflammatory drug (NSALD) or acetominophen.

58. The method of claim 57, which further comprises administering subsequent dosing periods with subsequent BTDS 20 dosage forms for a given time period as needed by the patient to achieve analgesia.

59. A method of treating a painful episode due to sickle cell anemia in a patient in need of such treatment, which method comprises administering to the patient BTDS 10 for 7 days with subsequent BTDS 20 dosage forms for a given time period as needed by the patient to achieve desired analgesia, wherein at least one BTDS dosage form is administered in combination with a non-steroidal anti-inflammatory drug (NSALD) or acetominophen.

60. The method of any one of claims 31, 41 or 43, wherein the NSALD is ibuprofen or aspirin.

* * * * *

UNITED STATES PATENT AND TRADEMARK OFFICE
CERTIFICATE OF CORRECTION

| | | |
|---|---|---|
| PATENT NO. | : 7,413,748 B2 | Page 1 of 1 |
| APPLICATION NO. | : 10/736049 | |
| DATED | : August 19, 2008 | |
| INVENTOR(S) | : Reidenberg et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 969 days.

Signed and Sealed this

Thirty-first Day of July, 2012

David J. Kappos
*Director of the United States Patent and Trademark Office*